(12) United States Patent
Chu et al.

(10) Patent No.: US 11,583,362 B2
(45) Date of Patent: Feb. 21, 2023

(54) DEVICES AND METHODS TO ACCESS A TARGET WITHIN THE BODY

(71) Applicant: Boston Scientific Limited, St. Michael (BB)

(72) Inventors: Michael S. H. Chu, Brookline, MA (US); Ashish Jain, Uttar Pradesh (IN); Subodh Morey, Goa (ID); Timothy P. Harrah, Cambridge, MA (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 0 days.

(21) Appl. No.: 16/640,602

(22) PCT Filed: Aug. 27, 2018

(86) PCT No.: PCT/US2018/048081
§ 371 (c)(1),
(2) Date: Feb. 20, 2020

(87) PCT Pub. No.: WO2019/046158
PCT Pub. Date: Mar. 7, 2019

(65) Prior Publication Data
US 2020/0352672 A1 Nov. 12, 2020

Related U.S. Application Data

(60) Provisional application No. 62/551,120, filed on Aug. 28, 2017.

(51) Int. Cl.
*A61B 90/11* (2016.01)
*A61B 17/34* (2006.01)
(Continued)

(52) U.S. Cl.
CPC .......... *A61B 90/11* (2016.02); *A61B 17/3403* (2013.01); *A61B 2017/00424* (2013.01);
(Continued)

(58) Field of Classification Search
CPC ......... A61B 90/10; A61B 90/11; A61B 90/13; A61B 2090/101; A61B 17/3403;
(Continued)

(56) References Cited

U.S. PATENT DOCUMENTS 5,649,946 A * 7/1997 Bramlet ......... A61B 17/320036
606/167
6,689,142 B1 * 2/2004 Tremaglio, Jr. ... A61B 17/3403
604/114
(Continued)

FOREIGN PATENT DOCUMENTS

DE 202008010644 U1 * 12/2009 ......... A61B 17/3403
DE 202008010644 U1 12/2009

OTHER PUBLICATIONS

International Search Report and Written Opinion for the International Application No. PCT/US2018/048081, dated Dec. 11, 2018, 10 pages.
(Continued)

*Primary Examiner* — Sarah A Simpson
(74) *Attorney, Agent, or Firm* — Seager, Tufte & Wickhem, LLP

(57) ABSTRACT

The present disclosure relates generally to the field of medical devices and establishing access to the renal capsule. In particular, the present disclosure relates to devices and methods for performing a percutaneous nephrolithotomy (PCNL) procedure accurately and efficiently while minimizing exposure of the medical professional to harmful radiation.

19 Claims, 14 Drawing Sheets

(51) Int. Cl.
*A61B 90/00* (2016.01)
*A61B 17/00* (2006.01)

(52) U.S. Cl.
CPC .............. *A61B 2017/00473* (2013.01); *A61B 2017/3407* (2013.01); *A61B 2017/3429* (2013.01); *A61B 2090/376* (2016.02); *A61B 2090/3966* (2016.02)

(58) Field of Classification Search
CPC .... A61B 2017/3405; A61B 2017/3407; A61B 2017/3409
See application file for complete search history.

(56) References Cited

U.S. PATENT DOCUMENTS

| | | | |
|---|---|---|---|
| 7,766,878 B2 | 8/2010 | Tremaglio, Jr. et al. | |
| 9,186,225 B1 | 11/2015 | Pettis | |
| 9,968,373 B1* | 5/2018 | Greenhalgh | A61B 17/3478 |
| 2010/0023065 A1* | 1/2010 | Welch | A61B 17/1703 |
| | | | 606/86 R |
| 2011/0184350 A1* | 7/2011 | McKay | A61B 17/3401 |
| | | | 604/174 |
| 2014/0257419 A1* | 9/2014 | Arthur | A61B 17/88 |
| | | | 606/86 R |
| 2014/0330277 A1* | 11/2014 | Ogrodnik | A61B 17/1725 |
| | | | 606/87 |
| 2014/0364861 A1* | 12/2014 | Easter | A61B 17/8875 |
| | | | 606/104 |
| 2015/0351861 A1* | 12/2015 | Pettis | A61B 90/39 |
| | | | 600/407 |
| 2016/0022292 A1* | 1/2016 | Stigall | A61F 2/013 |
| | | | 606/113 |
| 2017/0216494 A1* | 8/2017 | Roth | C22C 27/00 |
| 2018/0140312 A1* | 5/2018 | Sikora | A61B 17/1728 |
| 2018/0168746 A1* | 6/2018 | Swayze | A61B 17/3423 |
| 2018/0256201 A1* | 9/2018 | Greenhalgh | A61B 17/3403 |
| 2018/0256214 A1* | 9/2018 | Dejardin | A61B 17/7055 |
| 2018/0368862 A1* | 12/2018 | Jain | A61B 17/34 |
| 2019/0015131 A1* | 1/2019 | Hallisey | A61B 17/3403 |

OTHER PUBLICATIONS

International Preliminary Report on Patentability for the International Patent Application No. PCT/US2018/048081, dated Mar. 12, 2020, 6 pages.

\* cited by examiner

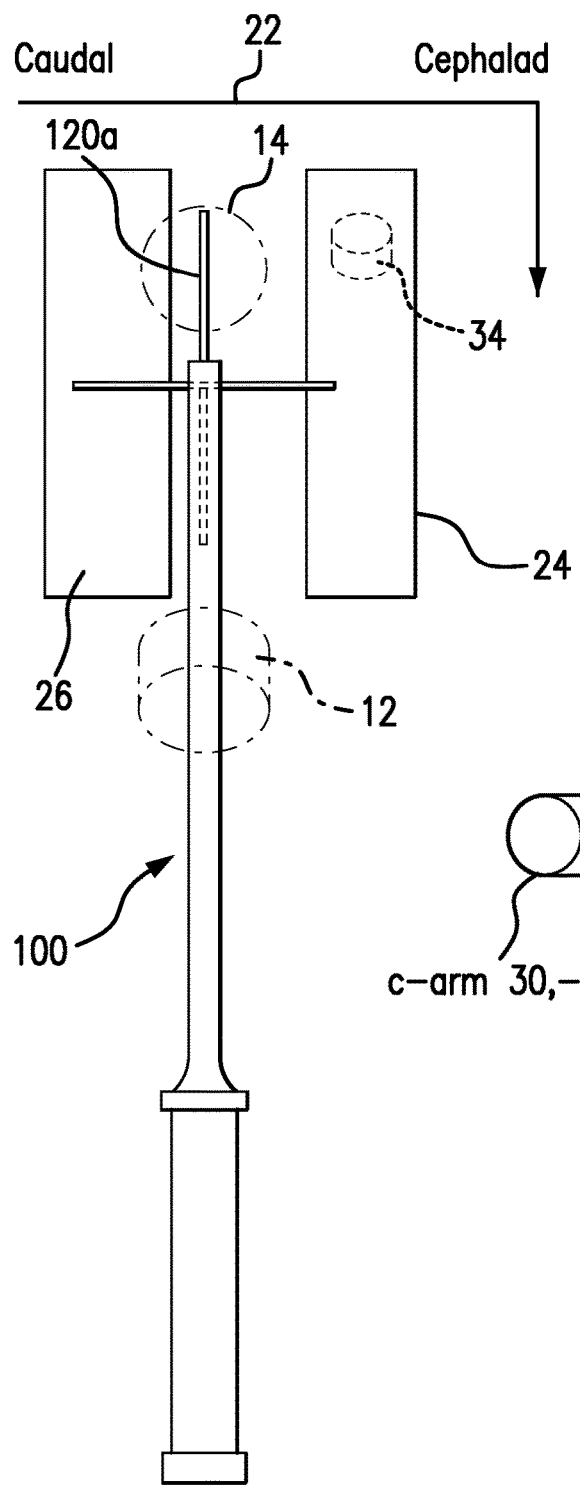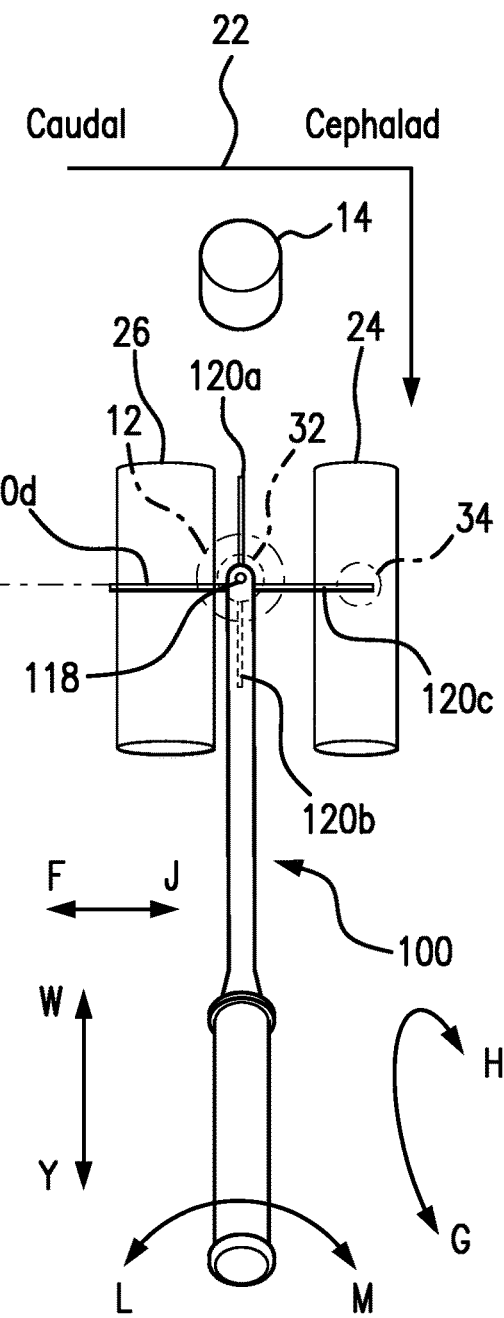
FIG. 8C
FIG. 8D

DEVICES AND METHODS TO ACCESS A TARGET WITHIN THE BODY

CROSS-REFERENCE TO RELATED APPLICATION

This application is a 371 U.S. National Stage of PCT Application No. PCT/US18/48081, filed Aug. 27, 2018, which claims the benefit of priority under 35 U.S.C. § 119 to U.S. Provisional Patent Application Ser. No. 62/551,120, filed on Aug. 28, 2017, each of which is incorporated by reference in its entirety for all purposes.

FIELD

The present disclosure relates generally to the field of medical devices and establishing access to a target within the body, such as placing an access needle into a renal capsule in the human body. In particular, the present disclosure relates to medical devices and methods for accurately and efficiently performing a percutaneous nephrolithotomy (PCNL) procedure, while minimizing exposure of the medical professional to harmful radiation. Various medical devices relating to establishing access to a target within the body are disclosed in U.S. Provisional Application Ser. No. 62/551,121, filed Aug. 28, 2017, entitled "Devices and Methods to Access a Target Within the Body," the entire contents of which are hereby incorporated by reference in their entirety for all purposes.

BACKGROUND

Using the kidney as a target example for establishing access, to accurately access the renal capsule during a percutaneous nephrolithotomy (PCNL) procedure, medical professionals are required to orient an access needle at the proper location and angle on the patient's skin, and then advance the access needle directly into a specific location of a calyx of the kidney and at a specific depth. To minimize their exposure to the potentially harmful fluoroscopic radiation beams required to visualize the kidney(s), medical professionals typically use tongs or forceps to grip the proximal end of the access needle as it is advanced through the patient's flank. Maintaining proper direction and/or orientation of the access needle during this step is often difficult due, at least in part, to the tendency of the access needle to bow or flex while being advanced, movement of the medical professional's hand, movement and breathing of the patient, etc.

A variety of advantageous medical outcomes may therefore be realized by the devices and/or methods of the present disclosure, which provide the combined benefits of establishing and maintaining proper access to a target within the body, e.g., needle orientation during a PCNL procedure, while minimizing the medical professional's exposure to harmful fluoroscopic radiation.

SUMMARY

In one aspect, the present disclosure relates to a medical device comprising an elongate shaft, wherein a distal portion of the elongate shaft may be angled relative to a longitudinal axis of the elongate shaft, and a lumen may extend through the angled distal portion. A first set of crosshairs may be disposed about a distal end of the distal portion of the elongate shaft. A portion of the distal portion of the elongate shaft, and the first set of crosshairs, may comprise a radiopaque material. The first set of crosshairs may include a first crosshair and a second crosshair extending along a plane parallel to the longitudinal axis, and a third crosshair and a fourth crosshair extending along a plane perpendicular to the longitudinal axis. The medical device may further include a second set of crosshairs disposed about a distal end of the distal portion of the elongate shaft, proximal to the first set of crosshairs. The second set of crosshairs may include a fifth crosshair and a sixth crosshair extending along a plane parallel to the longitudinal axis, and a seventh crosshair and an eighth crosshair extending along a place perpendicular to the longitudinal axis. Any of the first and/or second sets of crosshairs may include a radiopaque material. A length and/or width of the second set of crosshairs may be less than a length and/or width of the first set of crosshairs. The lumen may include a radiolucent silicone core. The radiolucent silicone core may be configured to receive an outer surface of an access needle.

In another aspect, the present disclosure relates to a medical device comprising an elongate shaft, wherein a distal portion of the elongate shaft may be angled relative to a longitudinal axis of the elongate shaft, a base may be attached to a distal end of the distal portion of the elongate shaft, and a lumen may extend through the base. A radiopaque ring may be disposed about an outer surface of the base. A portion of the base may include a radiolucent material. The radiopaque ring may be coaxial with the lumen. The lumen may comprise a radiolucent silicone core. The base may be permanently or removably attached to the elongate shaft. The base may include a slot extending from an outer surface of the base to the lumen. The radiolucent silicone core may be configured to receive an outer surface of an access needle. The base may include a slot extending from an outer surface of the base to the lumen.

In yet another aspect, the present disclosure relates to a medical device comprising a first arm comprising a proximal end and a distal end, a second arm comprising a proximal end and a distal end, a first base portion at the distal end of the first arm, and a second base portion at the distal end of the second arm. A first radiopaque ring may be disposed about a surface of the first base portion, and a second radiopaque ring may be disposed about a surface of the second base portion. The first base portion may include a first channel extending therethrough, and the second base portion may include a second channel extending therethrough. The distal end of the first arm may attached to the distal end of the second arm. The first and second base portions and the first and second ring portions may include a hemispherical shape. The first and second arms may be configured to move between a first position and a second position. With the first and second arms in the first position, the first and second base portions may be separated by a distance. With the first and second arms in the second position, the first and second base portions may contact each other such that the first and second channels form a lumen. The first and second base portions may be attached to the respective first and second arms at an angle, e.g., such that a longitudinal axis of the channels of the base portions may be oriented at an angle of approximately 30° relative to a longitudinal axis of the first and second arm. A portion of the first arm may overlap a portion of the second arm.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 8A-8D depict exemplary steps involved in performing a medical procedure using a needle guide, according to one embodiment of the present disclosure.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to medical devices and methods for accessing the renal capsule during a PCNL procedure, it should be appreciated that such devices and methods may be used in a variety of medical procedures, including, for example, deep brain surgeries, tissue sampling, tumor biopsies, tissue ablation procedures, etc.

As used herein, the term "C-arm" refers to a fluoroscopic X-ray system used to perform a variety of diagnostic imaging and minimally invasive surgical procedures. For example, a C-arm may be used by a medical professional to guide an access needle to a specific anatomical location while visualizing the access needle on an X-ray screen.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

Figure 1:
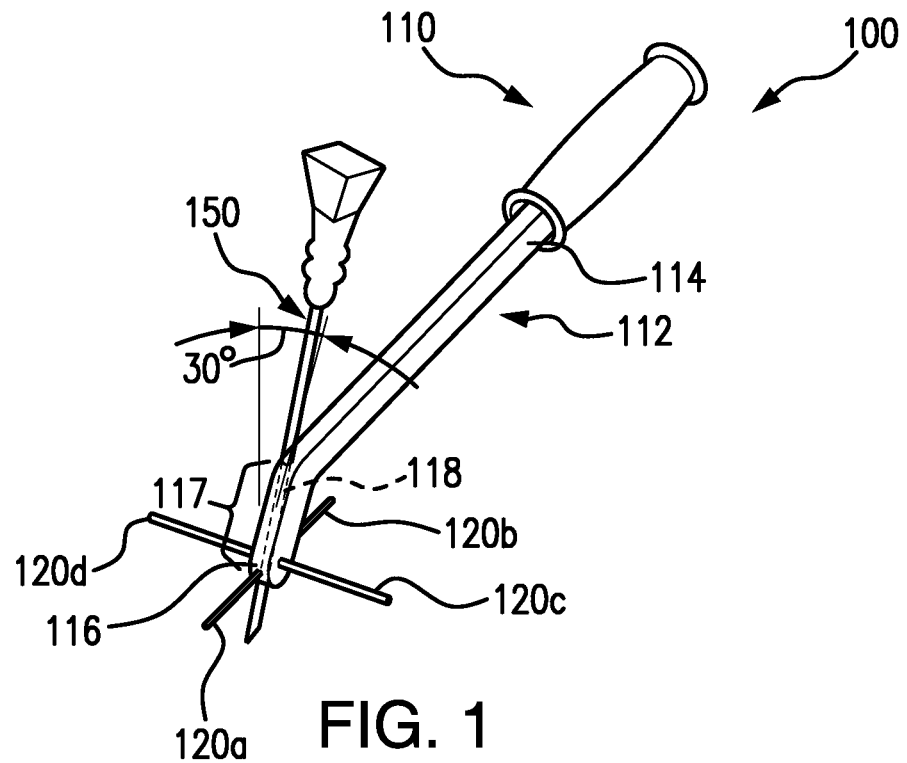
FIG. 1 provides a perspective view of a needle guide, according to one embodiment of the present disclosure.

In various embodiments, the present disclosure relates to devices and methods for positioning an access needle at a target location within the human body. Referring to FIG. 1, in one embodiment, a needle guide 100 of the present disclosure may include an elongate shaft 112 comprising a proximal end 114 and a distal end 116. The proximal end 114 of the elongate shaft 112 may be attached to a handle 110, and a distal portion 117 of the elongate shaft 112 may be bent or angled relative the remaining portion of the elongate shaft 112. For example, the distal portion 117 may include an angle of approximately 30° relative to a longitudinal axis of the elongate shaft 112. In one embodiment, the angled distal portion 117 may provide an ergonomic design which allows a medical professional to more easily rotate, twist or otherwise pivot the distal end 116 of the needle guide 100 on or along the patient's skin, to establish and/or maintain proper orientation with a specific (e.g., target) calyx of the kidney, as discussed below.

The angled distal portion 117 of the elongate shaft 112 may further include a lumen 118 extending through an approximate center portion thereof. The lumen 118 may be sized and configured to grip or receive the outer circumference of an access needle 150 with sufficient force to retain a position of the access needle within the needle guide 100 when not acted upon by an external force (e.g., force exerted by a medical professional), but to allow the access needle 150 to move or slide within/through the needle guide 100 when acted upon (e.g., retracted or extended) by an external force.

In various embodiments, portions of the elongate shaft 112, including portions of the distal portion 117, may be formed from or include a variety of radiopaque materials, (e.g., bismuth sulfate, metals, and/or polymers that include radiopaque fillers, powders, flakes, etc.). In one embodiment, the lumen 118 may comprise a non-radiopaque (e.g., radiolucent) silicone core (not shown), sized and configured to grip or receive the outer circumference of the access needle 150. The radiolucent silicone core and lumen 118 may serve as a bullseye through which the medical professional may visualize the target calyx under fluoroscopic imaging. Once the needle guide 100 is properly positioned on the surface of the patient's skin, the access needle 150 may be introduced into the lumen 118 and advanced to the target calyx, as discussed below.

In one embodiment, a needle guide 100 of the present disclosure may further include a first set of radiopaque crosshairs 120a-d positioned at, or near, the distal end 116 of the elongate shaft 112. The crosshairs 120a-d may be arranged in the form of a cross, such that crosshairs 120a and 120b are oriented along the same vertical plane as the elongate shaft 112 (e.g., having an axis parallel with a longitudinal axis of the elongate shaft 112), and crosshairs 120c and 120d are oriented on a plane perpendicular to the vertical plane (e.g., having an axis perpendicular to the longitudinal axis of the elongate shaft 112). The crosshairs 120a-d may be oriented such that an opening of the lumen 118 at the distal end 116 is located at an approximate center point of the elongate shaft 112 defined by an intersection of the axis of crosshairs 120a, 120b and the axis of crosshairs 120c, 120d.

Figure 2:
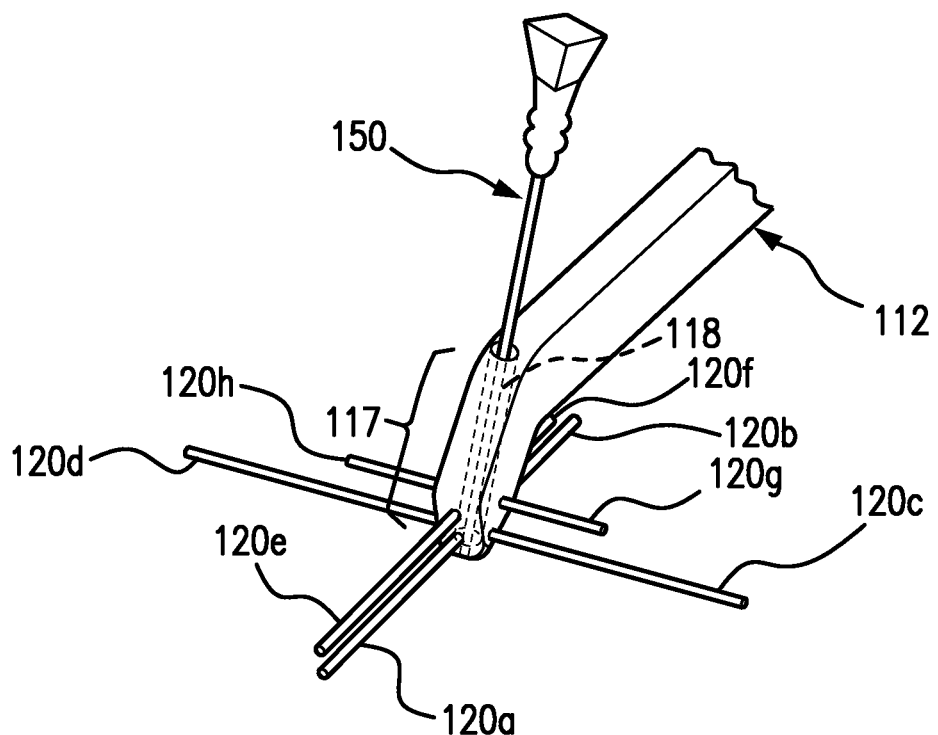
FIG. 2 provides a perspective view of a needle guide, according to one embodiment of the present disclosure.

Referring to FIG. 2, in one embodiment, a needle guide 100 of the present disclosure may include a second set of radiopaque crosshairs 120e-h positioned at, or near, the distal end 116 of the elongate shaft 112 proximal to (e.g., above) the first set of crosshairs 120a-d. The second set of crosshairs 120e-f may be shorter than corresponding crosshairs 120a-d, e.g., to avoid obscuring of the first set of crosshairs 120a-d during a medical procedure. In addition, or alternatively, a cross-sectional dimension of the second set of crosshairs 120e-h may be smaller than a cross-sectional dimension of the first set of crosshairs 120a-d to further prevent obscuring of crosshairs 120a-d and/or to distinguish between the first and second sets of crosshairs. The second set of crosshairs 120e-h may be arranged in the form of a cross similar to crosshairs 120a-d, e.g., crosshairs 120e and 120f oriented along the vertical plane and parallel to crosshairs 120a, 120b, and crosshairs 120g, 120h oriented on a plane perpendicular to the vertical plane and parallel to crosshairs 120c, 120d.

In various embodiments, the crosshairs 120a-d and/or 120e-h may be integrally formed on or within the distal end 116 of the elongate shaft 112, e.g., using injection molding techniques, as are commonly known in the art. In addition, or alternatively, the crosshairs 120a-d and/or 120e-h may be attached to the distal end 116 of the elongate shaft 112 after the needle guide 100 has been formed, e.g., using a suitable glue, adhesive, resin, solder and/or press fitting technique.

In various embodiments, either or both of the first and second sets of crosshairs may include fewer than four crosshairs. For example, crosshairs 120b and/or 120f may be excluded from the distal end 116 of the needle guide 100 due to the tendency of the elongate shaft 112 to shield or obscure these crosshairs, e.g., at a working angle of approximately 30°. In addition, or alternatively, the present disclosure is not limited to four or fewer crosshairs or being arranged in the shape of a cross, but may include, for example, an odd or even number of crosshairs higher than four and/or a variety of symmetrical or asymmetrical configurations, e.g., Y-shapes, triangular shapes, etc.

In various embodiments, the radiopaque crosshairs 120a-d and/or 120e-h may be made from a super-elastic material (e.g., nitinol wire, coil or spring, etc.), or thin metallic material (e.g., stainless steel wire, coil or spring,) to allow each crosshair to individually flex when pressed against the patient's skin without permanently deforming. In other embodiments, the crosshairs 120a-d and/or 120e-h may be molded from a polymeric material. The metallic and polymer materials may include a radiopaque filler or may be coated with or include a covering of radiopaque material, as discussed above.

Although the elongate shaft 112 of FIG. 1 includes a substantially rectangular cross-section, in various other embodiments, the elongate shaft 112 may include a variety of cross-sectional dimensions, including, for example, oval, circular, triangular, oblong, square and combinations or iterations thereof.

Although the elongate shaft 112 of FIG. 1 includes an angled distal portion 117, in various embodiments, the elongate shaft 112 may be substantially straight along the entire longitudinal axis, and include a lumen 118 extending at an angle through the distal portion 117, e.g., an angle of approximately 30° relative to a longitudinal axis of the elongate shaft 112.

Referring to FIGS. 3A-3G, in one embodiment, a needle guide 200 of the present disclosure may include an elongate shaft 212 comprising a proximal end 214 and a distal end 216. The proximal end 214 of the elongate shaft 212 may be attached to a handle 210, and the distal end 216 of the elongate shaft 212 may be permanently or reversibly attached to a base 230. The elongate shaft 212 may include an angled or bent portion 217a, e.g., angled approximately 30 degrees to approximately 45° relative to a longitudinal axis of the elongate shaft, between parallel portions 217b, 217c of the elongate shaft 212. In one embodiment, the angled portion 217a may provide an ergonomic design which allows a medical professional to more easily rotate, twist, pivot or otherwise transfer force to the base 230 on or along the patient's skin, for improved stability and to establish and/or maintain proper orientation with the target calyx.

Figure 3A:
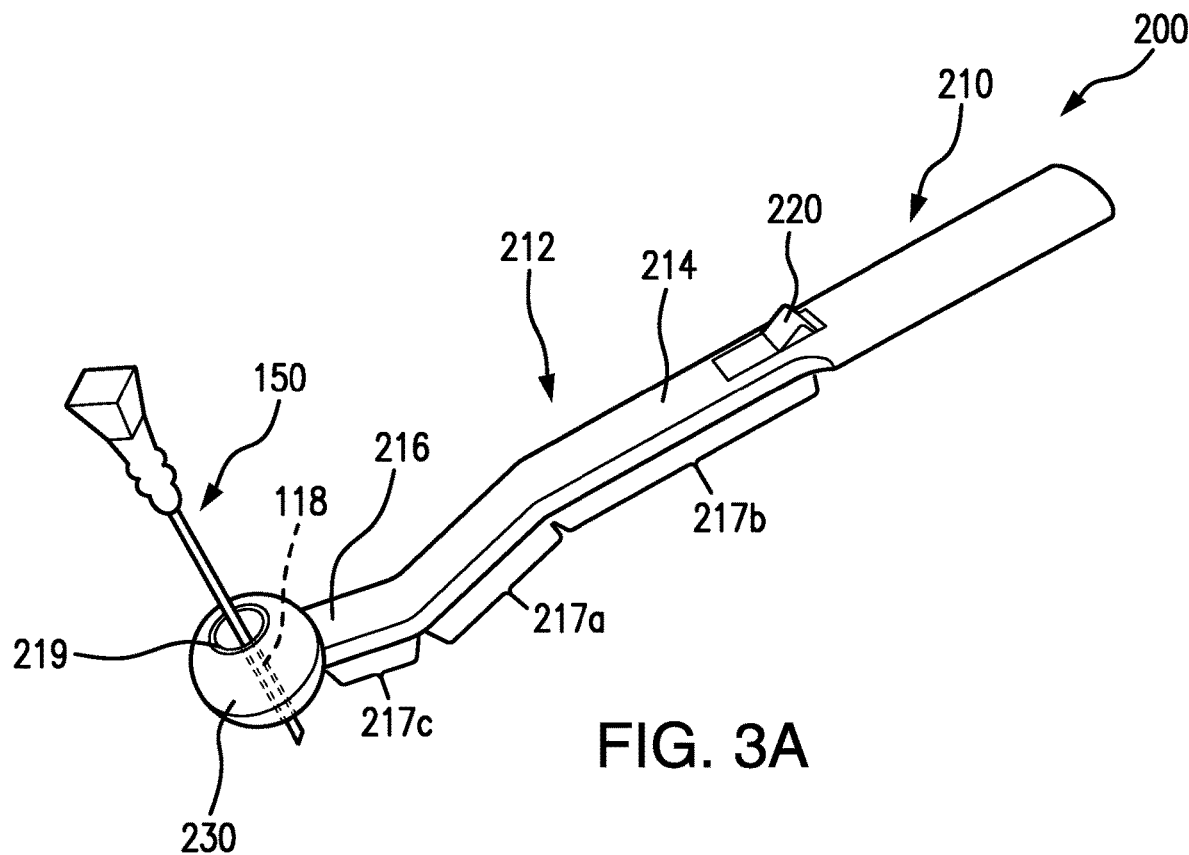
FIGS. 3A-3H provide perspective views of a needle guide, according to one embodiment of the present disclosure.
Figure 3B:
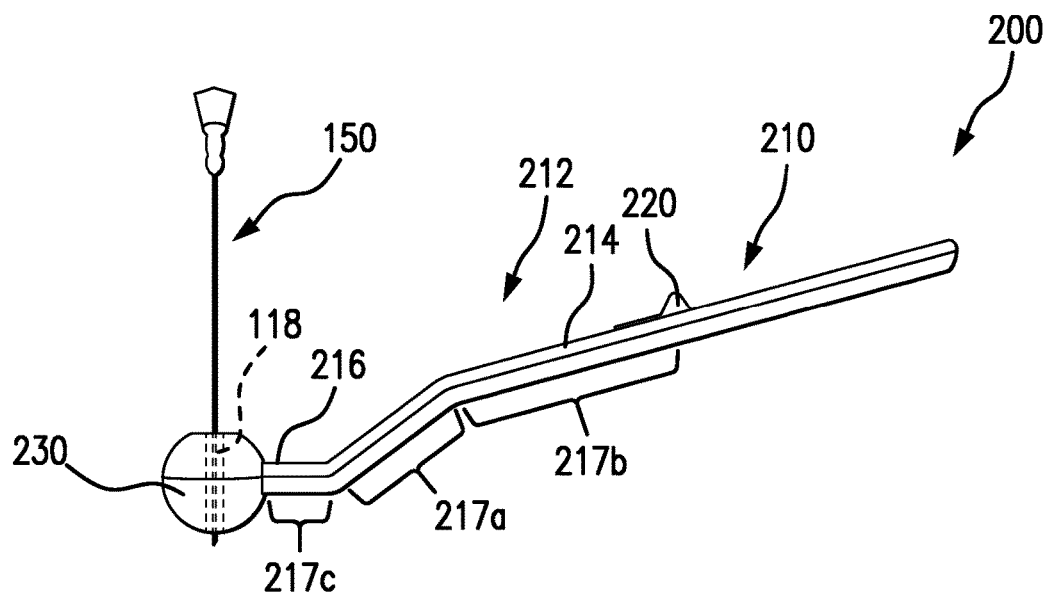
Figure 3C:
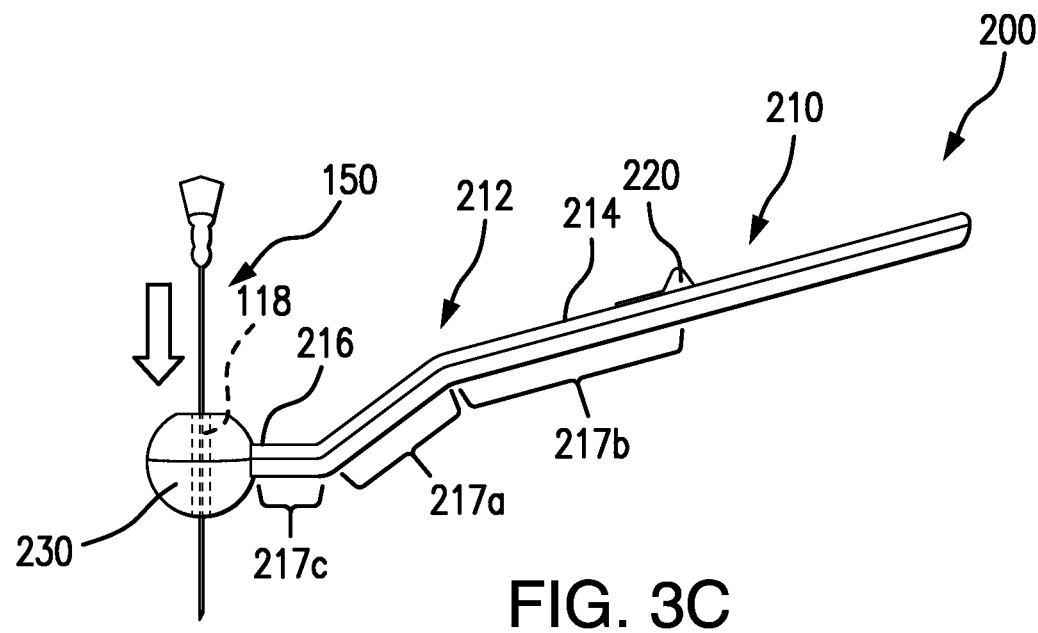

In one embodiment, the base 230 may include an outer surface with a substantially round shape and a lumen 218 extending through an approximate center portion thereof. In various other embodiments, the elongate shaft 212 may be substantially straight along its entire length, and/or the lumen 218 may be formed within the base 230 at an appropriate angle to provide the proper orientation for accessing the target calyx. In various other embodiments, the base 230 may include a variety of shapes other than round, including, for example, oblong, triangular, square, rectangular and combinations or iterations thereof. In one embodiment, the lumen 218 may comprise a radiolucent silicone core (FIG. 3A), sized and configured to grip or receive the outer circumference of an access needle 150 with sufficient force to retain a position of the access needle within the base 230 when not acted upon by an external force (e.g., force exerted by a medical professional), but to allow the access needle 150 to move or slide within/through the base 230 when acted upon (e.g., retracted or extended) by an external force (FIG. 3C). A ring or band 219 comprising a radiopaque material, e.g., bismuth sulfate, metals, and/or polymers that include radiopaque fillers, powders, flakes, etc., may be disposed on or within the base, e.g., around the silicone core and/or lumen 218. In various embodiments, portions of the base 230 may be formed from or include a variety of radiolucent materials, such that the radiopaque (RO) ring 219 may serve as a bullseye through which the medical professional may visualize the radiopaque access needle (e.g., centered within the RO ring) and target calyx under fluoroscopic imaging. Alternatively, the needle guide 200 may be positioned on the patient's skin without the access needle 150 disposed within the lumen 218. The RO ring 219 may serve as a bullseye through which the medical professional may visualize the target calyx under fluoroscopic imaging. Once the needle guide 200 is properly positioned on the patient's skin, the access needle 150 may be introduced into the lumen 118 and advanced to the target calyx, as discussed below.

Figure 3D:
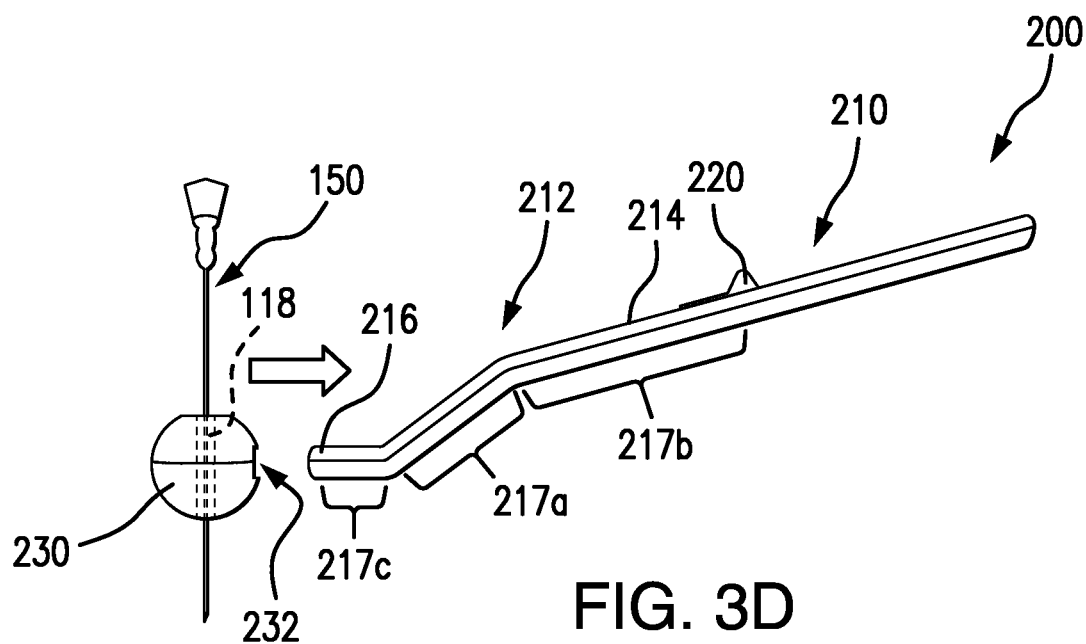
Figure 3E:
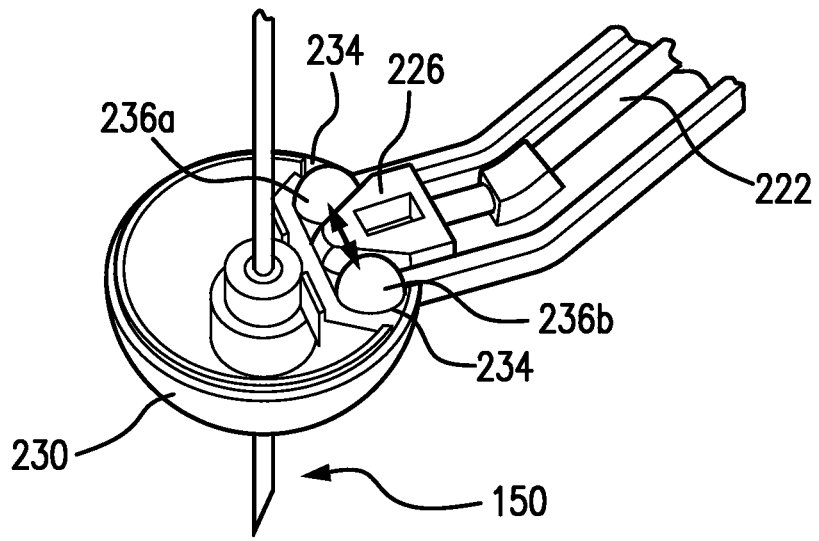
Figure 3F:
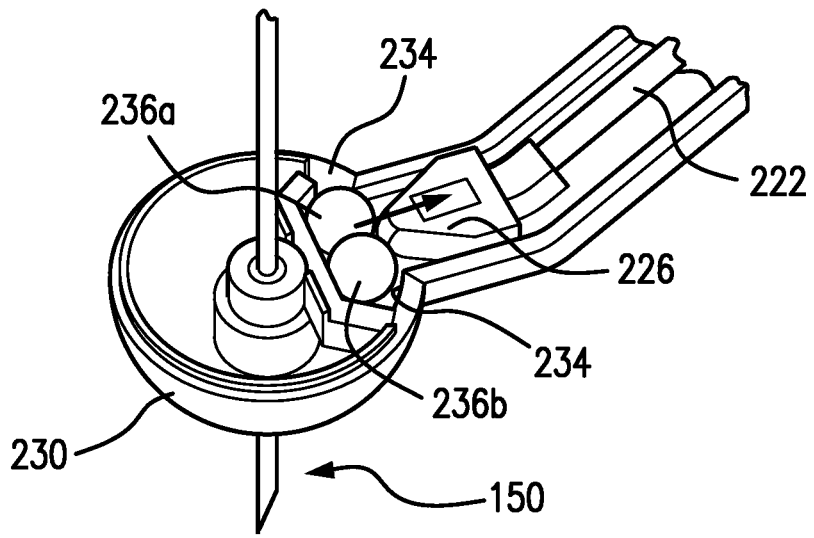

In one embodiment, the base 230 may include a recessed portion 232 configured to reversibly receive the distal end 216 of the elongate shaft 212 (FIG. 3D). A release mechanism may be incorporated within the handle 210, or proximal portion of the elongate shaft 212, to effectuate separation of the base 230 from the distal end 216 elongate shaft 212. For example, a mechanical release mechanism may include a release lever 220 incorporated within a proximal portion of the elongate shaft 212 (e.g., near the handle 210) and connected to an actuatable member 222 (FIG. 3E-3F) which extends along an inner length of the elongate shaft. The actuatable member 222 may include a proximal end (not shown) operably attached to the release lever 220, and a tapered distal end 226. A pair of moveable bearings 236a, 236b may be disposed within the recessed portion 232 of the base 230. With the release lever 220 in a first (e.g., forward) position, the actuatable member 222 may be maintained in an extended configuration such that the tapered distal end 226 maintains moveable bearings 236a, 236b in a separated configuration to engage an inner surface 234 of the base 230, thereby maintaining the base 230 and elongate shaft 212 in a locked configuration (FIG. 3E). With the release lever 220 moved from the first position to a second (e.g., retracted)

position, the tapered distal end 226 may be removed from between the bearings 236a, 236b, thereby allowing bearings 236a, 236b to move toward each other and disengage the inner surface 234 of the base 230 (FIG. 3F).

Figure 3G:
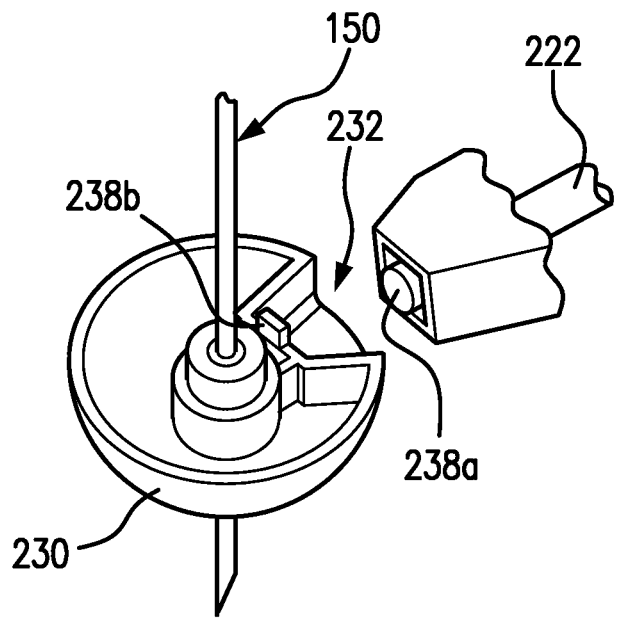

Alternatively, referring to FIG. 3G, a magnetic release mechanism may include a release lever 220 incorporated within a proximal portion of the elongate shaft 212 (e.g., near the handle 210) and connected to an actuatable member 222 which extends along an inner length of the elongate shaft. The actuatable member 222 may include a proximal end (not shown) operably attached to the release lever 220, and a distal end 226 comprising a first magnet 238a. The recessed portion 232 of the base 230 may include a corresponding second magnet 238b with a polarity opposite that of the first magnet 238a. With the release lever 220 in a first (e.g., forward) position, the actuatable member 222 may be maintained in an extended configuration such that the first magnet 238a engages the corresponding second magnet 238b, thereby maintaining the base 230 and elongate shaft 212 in a locked configuration. The release lever 220 may be moved from the first position to a second (e.g., retracted) position with sufficient force to overcome the magnetic interaction between the first and second magnets 238a, 238b and disengage the elongate shaft 212 from the base 230.

Figure 3H:
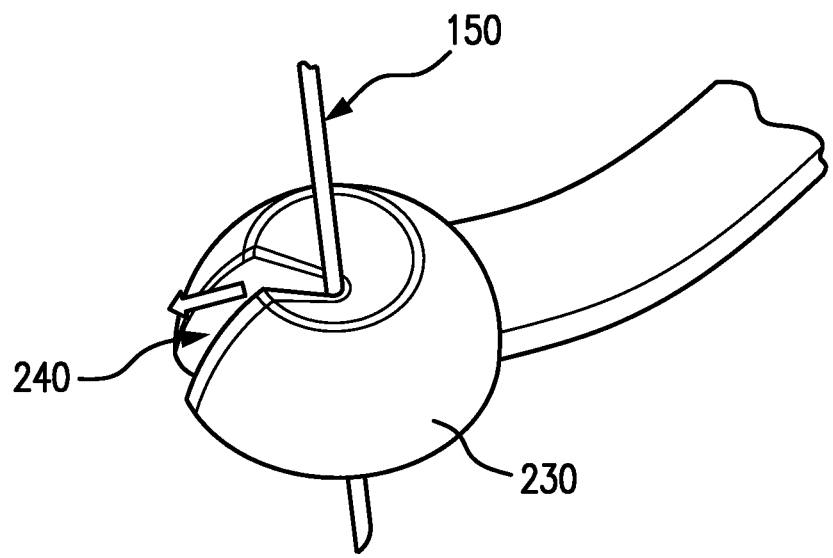

In various embodiments, the base 230 may be disengaged from the distal end 216 of the elongate shaft 212 after the access needle 150 is properly positioned within the target calyx to reduce the amount of force exerted on the access needle and/or minimize the likelihood of accidental contact with the elongate shaft 212 and/or handle 210 imparting trauma to the target calyx. Similarly, referring to FIG. 3H, in one embodiment, the base 230 may include a slot 240 extending through the base to the lumen 218. After the access needle 150 has been properly positioned within the target calyx, the base 230 may be separated (either alone or attached to the elongate shaft) from the access needle 150 by sliding the base 230 so that the access needle 250 passes through the slot 240.

Figure 4A:
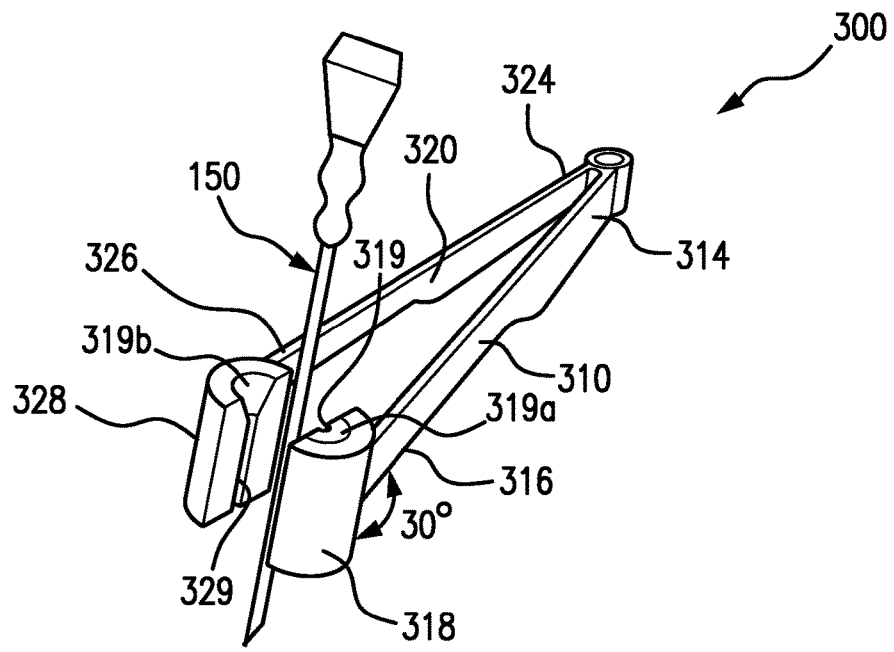
FIGS. 4A-4D provide perspective views of a needle guide, according to one embodiment of the present disclosure.
Figure 4B:
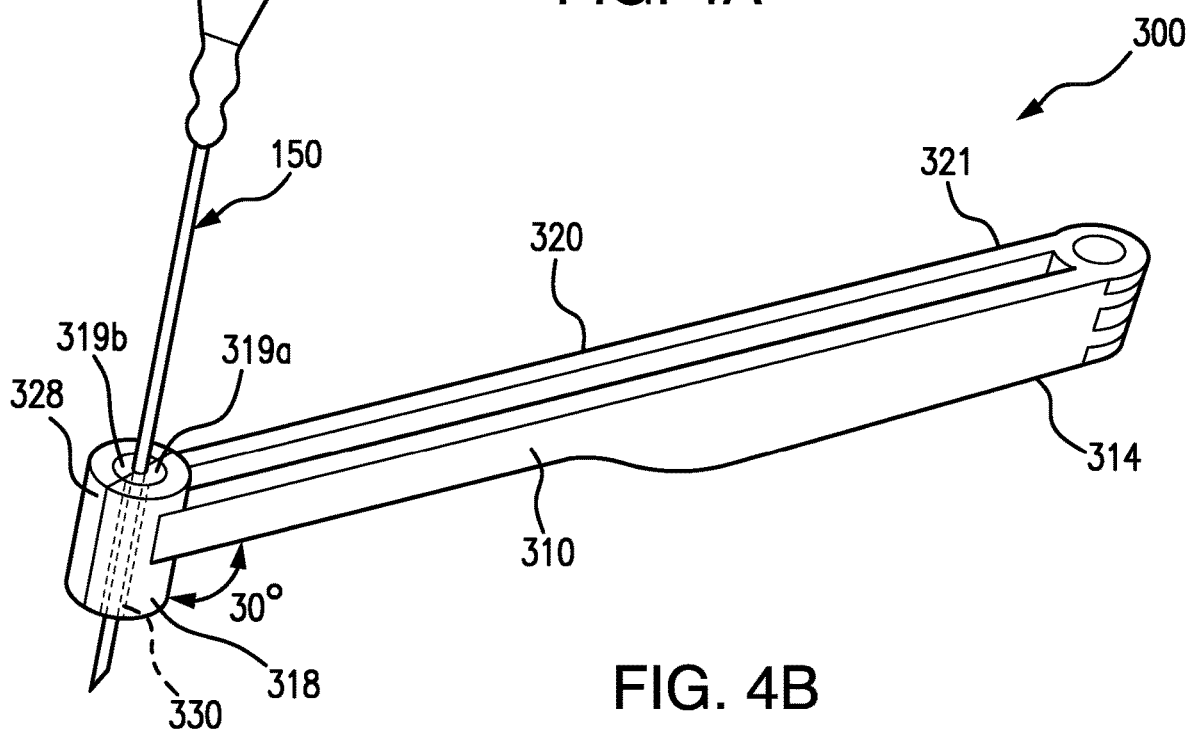
Figure 4C:
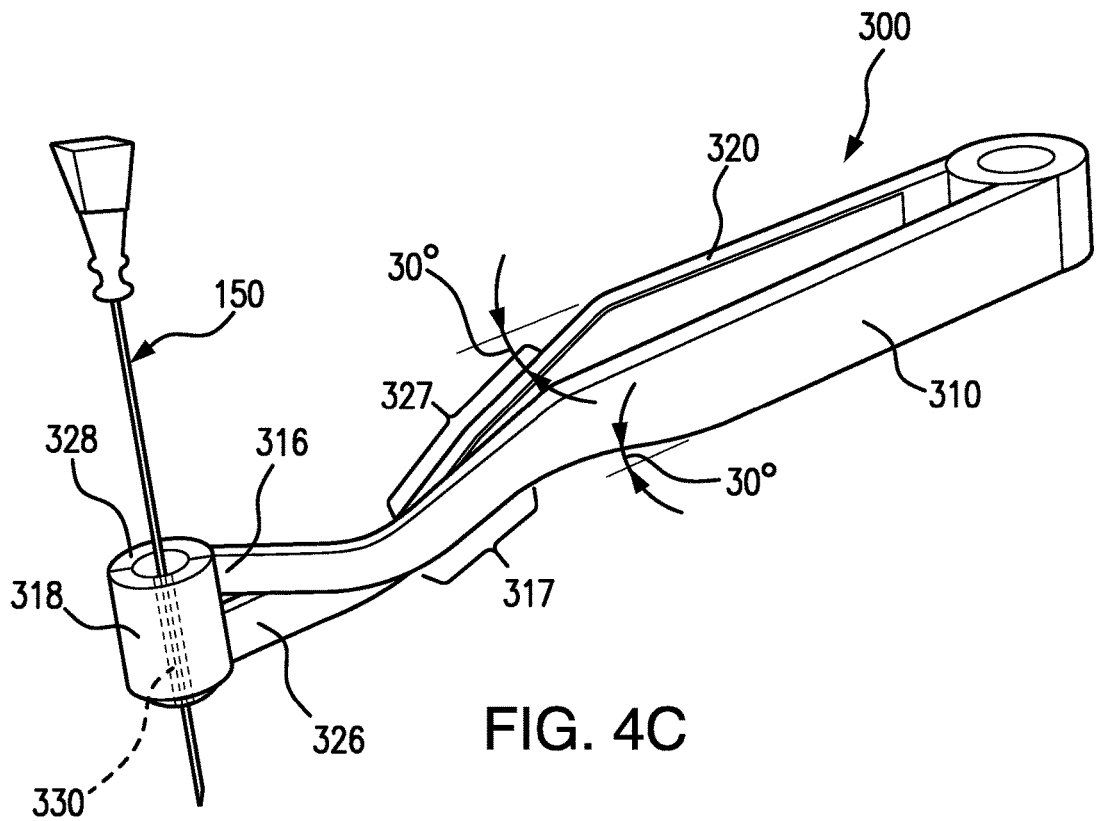

Referring to FIGS. 4A-4C, in one embodiment, a needle guide 300 of the present disclosure may include a first arm 310 comprising a proximal end 314 and a distal end 316. The distal end 316 of the first arm 310 may include a first base portion 318 extending from the first arm. The base portion 318 may have a substantially hemispherical cross-section defining a first channel 319 along a length thereof. In one embodiment, the first base portion 318 may extend from the distal end 316 of the first arm 310, e.g., an axis of the first channel 319 may be oriented at an angle of approximately 30° to approximately 45° relative to a longitudinal axis of the first arm 310. The needle guide 300 may further include a corresponding second arm 320 comprising a proximal end 324 and a distal end 326. The distal end 326 of the second arm 320 may include a second base portion 328 extending from the first arm. The second base portion may have a substantially hemispherical cross-section defining a second channel 329 along a length thereof. In one embodiment, each of the first and second channels 319, 329 may comprise a radiolucent silicone core. In one embodiment, the second base portion 328 may extend from the distal end 326 of the second arm 320, e.g., an axis of the channel 329 may be oriented at an angle of approximately 30° to approximately 45° relative to a longitudinal axis of the second arm 320. The proximal ends 314, 324 of the first and second arms 310, 320 may be pivotally, bendably and/or flexibly connected or biased (e.g., spring loaded) such that the needle guide 300 may move between a first (e.g., open) position in which the first and second base portions 318, 328 are separated by a distance, and a second (e.g., closed) position in which the first and second base portions 318, 328 are placed in contact with each other. In the second position, the first and second channels 319, 329 of the respective first and second base portions 318, 328 may align to form an open lumen 330 therethrough. The lumen may be contiguous.

In one embodiment, the open lumen 330 may be sized and configured to grip or receive the outer circumference of an access needle 150 with sufficient force to retain a position of the access needle within the corresponding first and second base portions 318, 328 when not acted upon by an external force (e.g., force exerted by a medical professional), but to allow the access needle 150 to move or slide within/through the combined first and second base portions 318, 328 when acted upon (e.g., retracted or extended) by an external force. A first and second hemispherical ring or band 319a, 319b comprising a radiopaque material, e.g., bismuth sulfate, metals, and/or polymers that include radiopaque fillers, powders, flakes, etc., may be disposed on or within the respective first and second base portions 318, 328 to define a circular or cylindrical radiopaque ring or band (e.g., at the openings of the lumen or along the length of the lumen) when the first and second arms 310, 320 are in the second position. In various embodiments, portions of the first and second base portions 318, 328, and/or portions of the first and second arms 310, 320, may be formed from or include a variety of radiolucent materials, such that the radiopaque (RO) ring may serve as a bullseye through which the medical professional may visualize the radiopaque access needle (e.g., centered within the RO ring) and target calyx under fluoroscopic imaging. Alternatively, the needle guide 300 may be positioned on the patient's skin without the access needle 150 disposed within the open lumen 330. The RO ring may serve as a bullseye through which the medical professional may visualize the target calyx under fluoroscopic imaging. Once the needle guide 300 is properly positioned on the patient's skin, the access needle 150 may be introduced into the open lumen 330 and advanced to the target calyx, as discussed below.

In various embodiments, the first and second arms 310, 320 may be connected at respective proximal ends 314, 324 by a suitable hinge mechanism, as are commonly known in the art. In addition, or alternatively the first and second arms 310, 320 may be formed from a single piece of material that may be bent, molded, shaped or otherwise formed into a configuration as depicted in FIGS. 4A-4C. In one embodiment, an external force (e.g., the force applied by the fingers of a medical professional) may move the first and second arms 310, 320 from the first (e.g., open) position to the second (e.g., closed) position. Stated differently, the needle guide 300 may be biased to assume the first position when in a relaxed (e.g., natural, resting, default) state. In another embodiment, an external force may move the first and second arms 310, 320 from the second (e.g., closed) position to the first (e.g., open) position. Stated differently, the needle guide 300 may be biased to naturally assume the second position when in a relaxed (e.g., natural, resting, default) state.

Figure 4D:
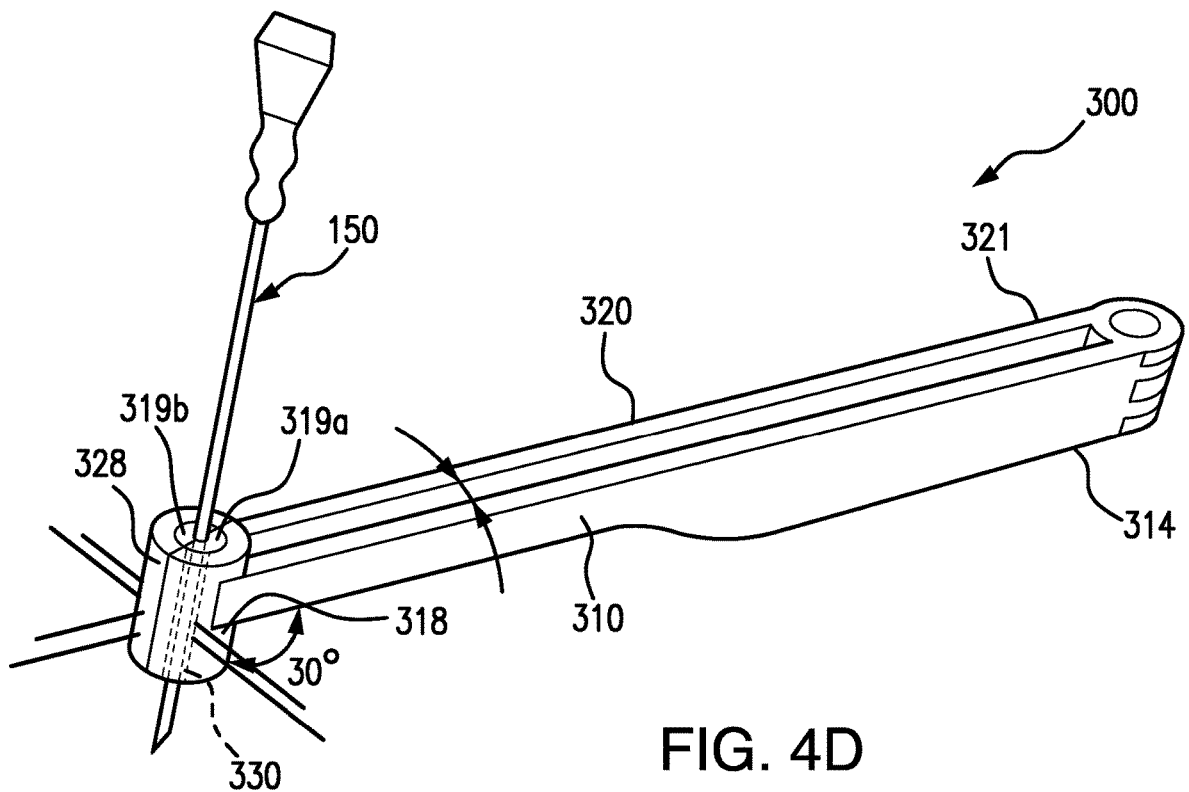

Referring to FIG. 4C, in one embodiment, the first and second base portions 318, 328 may extend substantially perpendicular from the respective distal ends 316, 326 of the first and second arms 310, 320. A distal portion 317, 327 of the first and second arms 310, 320 may include corresponding angled or bent portions, which cross or overlap in a scissor-like configuration. For example, the distal portion 317 of the first arm 310 may extend at an angle of approximately 30° relative to a longitudinal axis of the first arm 310, and the distal portion 327 of the second arm 320 may extend at an angle of approximately 30° relative to a longitudinal axis of the second arm 320. Referring to FIG. 4D, in one embodiment, a needle guide 300 of the present disclosure may further include a first set of crosshairs (e.g., 120a-d as depicted in FIG. 1) or first and second sets of crosshairs (e.g., 120a-d and 120e-h as depicted in FIG. 2).

In various embodiments, the angled first and second base portions 318, 328 (FIGS. 4A-4B), and the angled distal portion 317, 327 of the respective first and second arms 310, 320 (FIG. 4C) may provide an ergonomic design which may allow a medical professional to more easily rotate, twist or otherwise pivot the combined first and second base portions 318, 328 on or along the patient's skin, to establish and/or maintain proper orientation with a target calyx.

Figure 5:
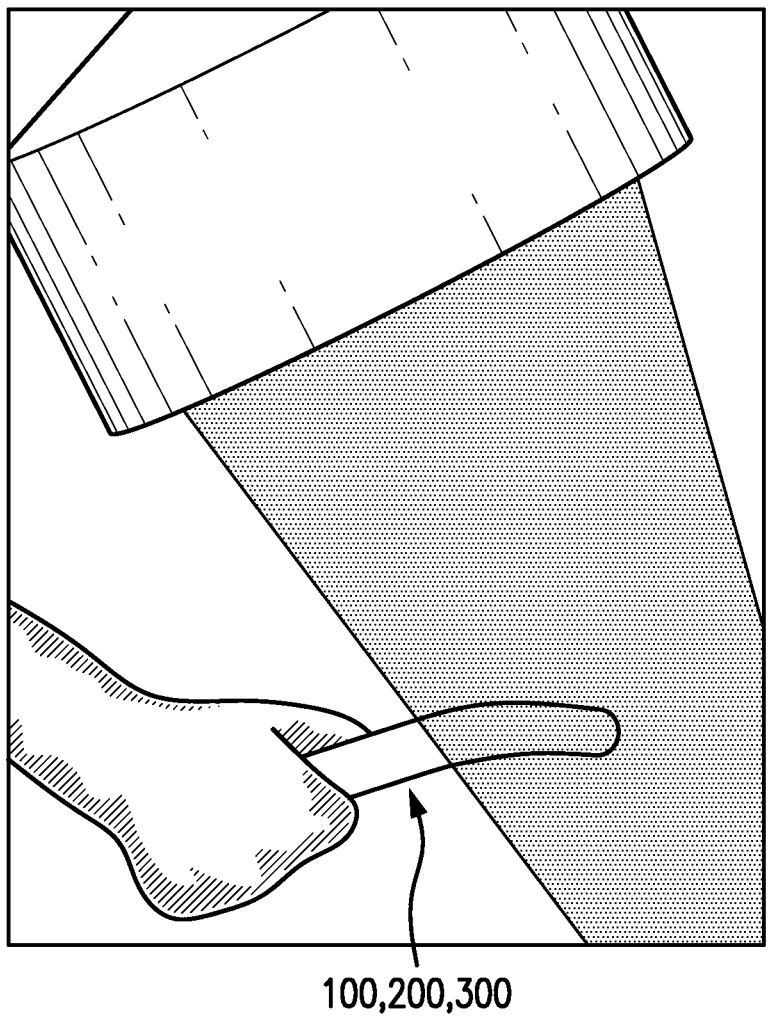
FIG. 5 provides a schematic illustration of a needle guide in use during a medical procedure, according to one embodiment of the present disclosure.

Referring to FIG. 5, in various embodiments, any of the needle guides 100, 200, 300 disclosed herein may include an elongate shaft 112, 212 (FIGS. 1-3H), or first and second arms 310, 320 (FIGS. 4A-4D), with a sufficient length (e.g., at least 10 inches or more, at least 15 inches or more, at least 20 inches or more) to allow a medical professional to position the angled distal portion 117 (FIGS. 1-2), base 230 (FIGS. 3A-3H) or combined first and second base portions 318, 328 (FIGS. 4A-4D) at a desired location on a patient's skin without exposing a medical professional's hand(s) or arm(s) to a radiation beam emitted from a fluoroscope during a medical procedure.

In various embodiments, the handle 110, 210 of needle guides 100, 200 of the present disclosure may be permanently or releasably attached to the elongate shaft 112, 212.

Although the needle guides 100, 200, 300 of the present disclosure are generally disclosed as being configured to align respective lumens 118 (FIG. 1), 218 (FIG. 3A-3D), 330 (FIG. 4C) to match the corresponding 30° angle of a C-arm (e.g., C-arm 30 degree lateral, 0 degree caudal), in various embodiments, the lumens may be configured to match or accommodate a variety of C-arm angles (e.g., in a range between 0° and 50°). In various embodiments, the silicone core defining the lumens 118, 218, 330 of needle guides 100, 200, 300, or other cores or lumens, of the present disclosure may further include a radiopaque coil disposed therein, and through which the medical professional may visualize the target calyx under fluoroscopic imaging (e.g., prior to introducing the access needle 150).

Figures 6A, 6B:
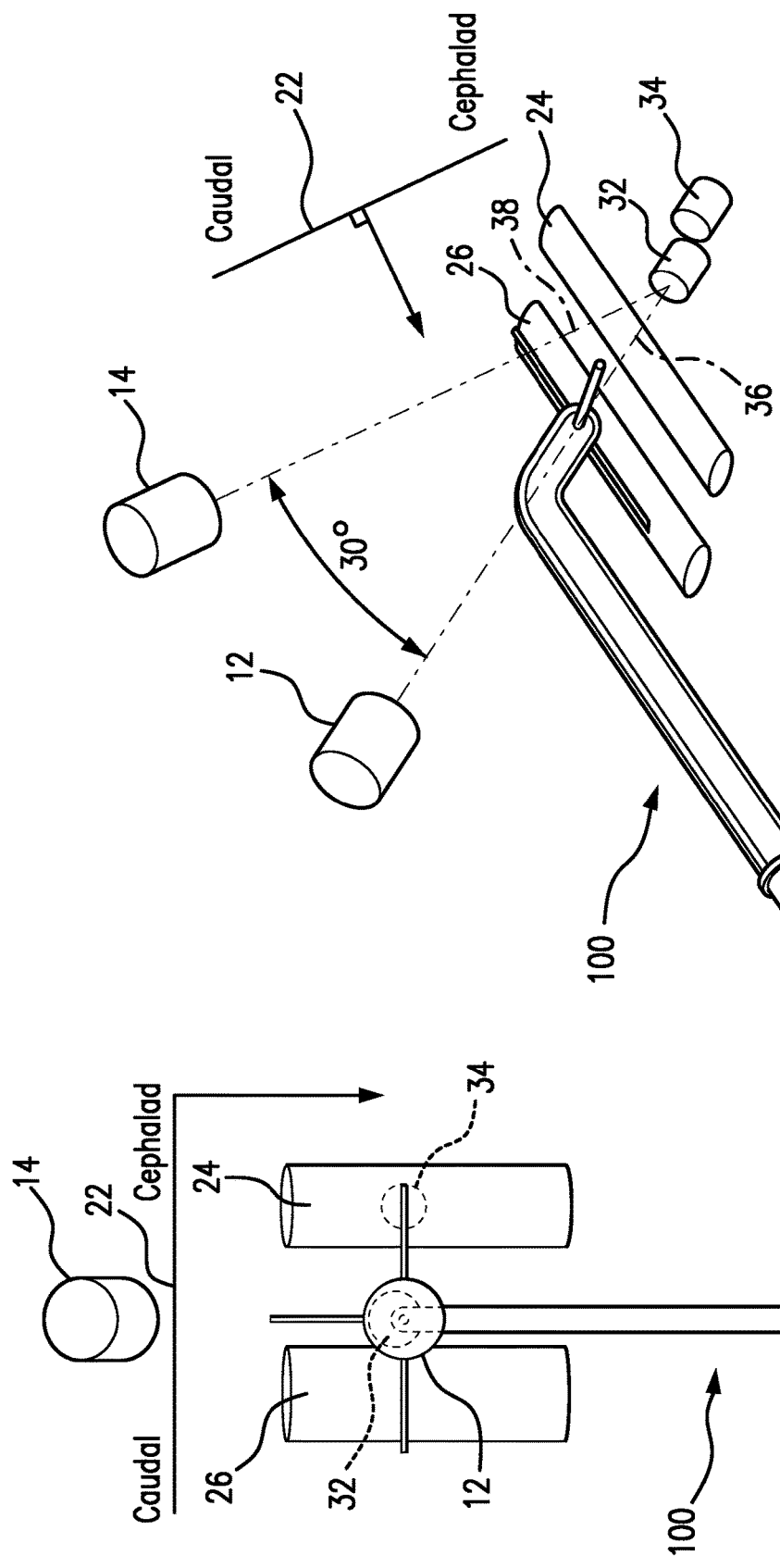
FIGS. 6A-6B provide perspective views of a needle guide oriented to align with an unobstructed calyx, according to one embodiment of the present disclosure.

FIG. 6A provides an exemplary perspective view of a needle guide 100 positioned on the patient's flank between the eleventh and twelfth ribs 24, 26, with the C-arm rotated between two positions relative to a lateral central line (e.g., perpendicular to the spine 22) between the caudal (posterior) and cephalad (anterior) ends of the patient. A first position 12 of the C-arm may be 30° lateral and 0° caudal, (e.g., C-arm 30,0). A second position 14 of the C-arm may be 0° lateral and 0° caudal, (e.g., C-arm 0,0). FIG. 6B provides an alternative perspective view of a needle guide 100 perpendicular to the C-arm 30,0 orientation of FIG. 6A. By way of example, FIGS. 6A and 6B depict first and second calyces 32, 34 located at different portions of a kidney (not shown). For demonstration purposes, the first and second calyces 32, 34 are located approximately the same distance from the spine 22 and at approximately the same depth. Dotted line 36 indicates a projected trajectory (e.g., needle path) to the first calyx 32, and dotted line 38 indicates a projected trajectory to the second calyx 34 as viewed from C-arm 30,0 through the lumen of the needle guide. As indicated by dotted line 36, the projected needle path to the first calyx 32 is not obstructed by the eleventh rib 24, and the projected needle path to the second calyx 34 is obstructed by the eleventh rib 24.

Figure 7A:
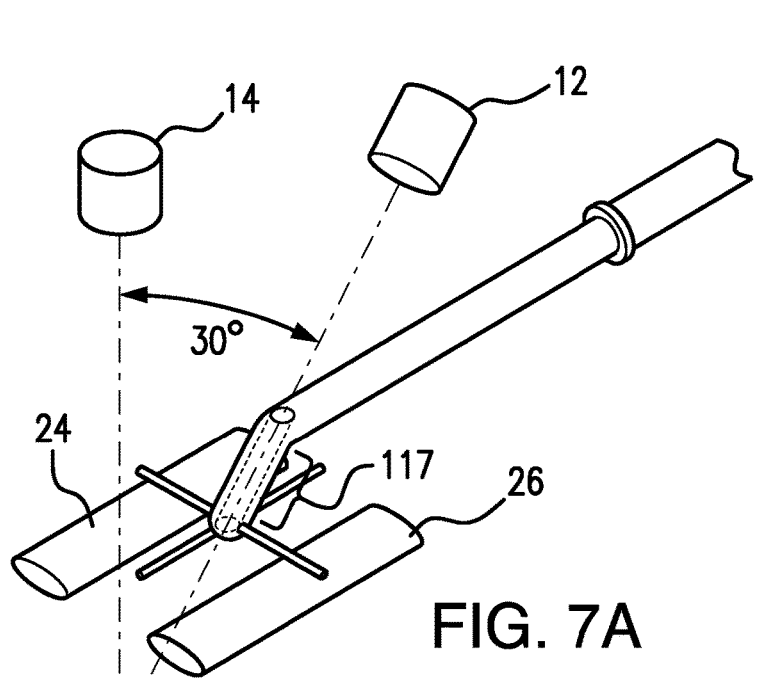
FIGS. 7A-7F depict exemplary steps involved in performing a medical procedure using a needle guide, according to one embodiment of the present disclosure.
Figure 7B:
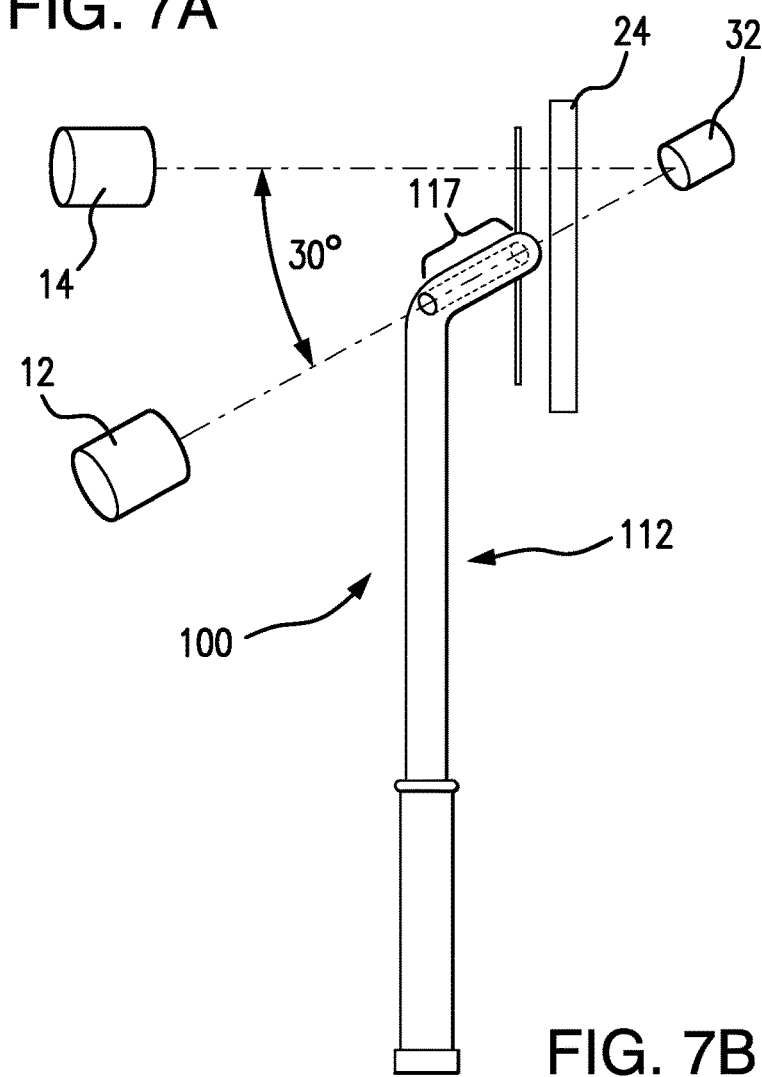
Figure 7C:
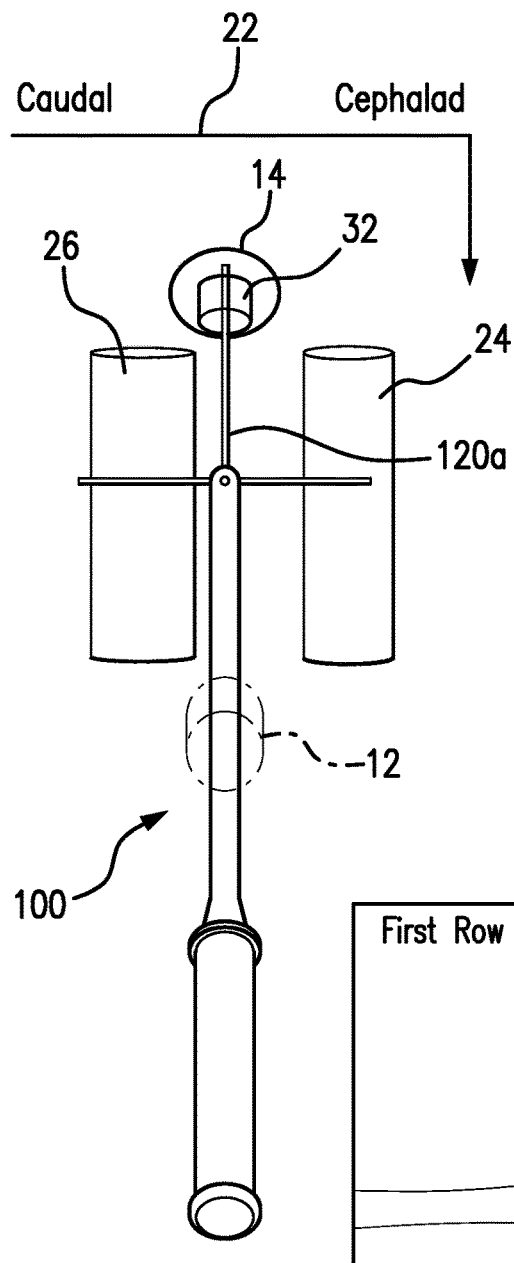
Figure 7D:
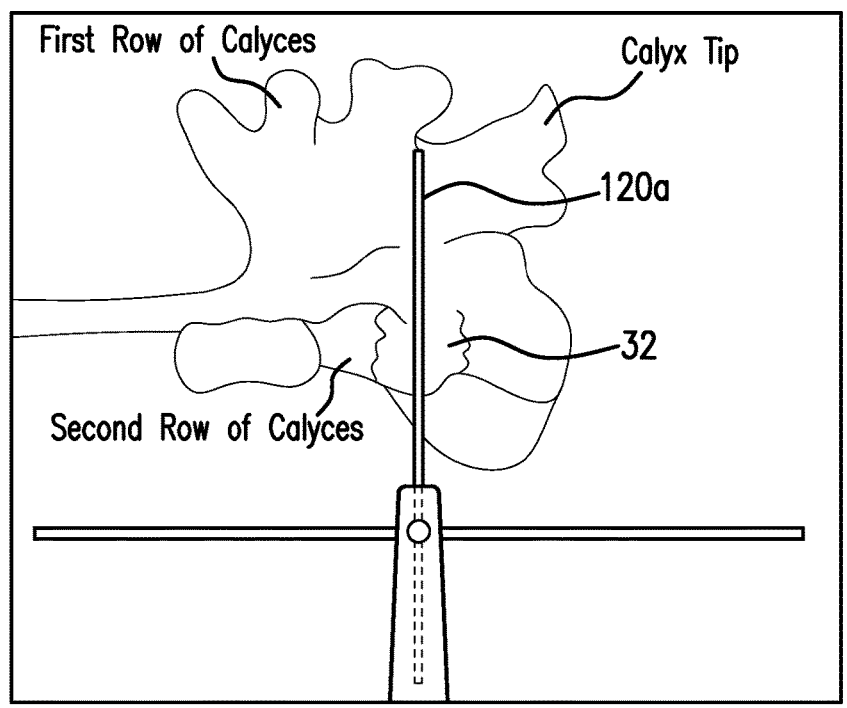

FIGS. 7A-7G provide exemplary steps involved in accessing an unobstructed calyx using a needle guide 100, in accordance with one embodiment of the present disclosure. FIG. 7A provides a perspective view of a first calyx 32 that is not obstructed by the eleventh or twelfth ribs 24, 26. The projected needle path to the unobstructed first calyx 32 may be established by an X-ray energy beam emitted from a C-arm rotated between the C-arm 0,0 and C-arm 30,0 positions 14, 12. As depicted in the perspective side view of FIG. 7B, the positions C-arm 0,0 and C-arm 30,0 may be separated by an angle of approximately 30° in the lateral direction. This angle may substantially align with the 30° angle of the distal portion 117 of the elongate shaft 112 when the needle guide 100 is held in a horizontal position. As depicted in the anterior/posterior (A/P) view of FIG. 7C, as viewed from the C-arm 0,0 position, crosshair 120a of the needle guide 100 may intersect, and represent a needle trajectory to, the first calyx 32. FIG. 7D provides a schematic representation of crosshair 120a intersecting the first calyx 32.

Figure 7E:
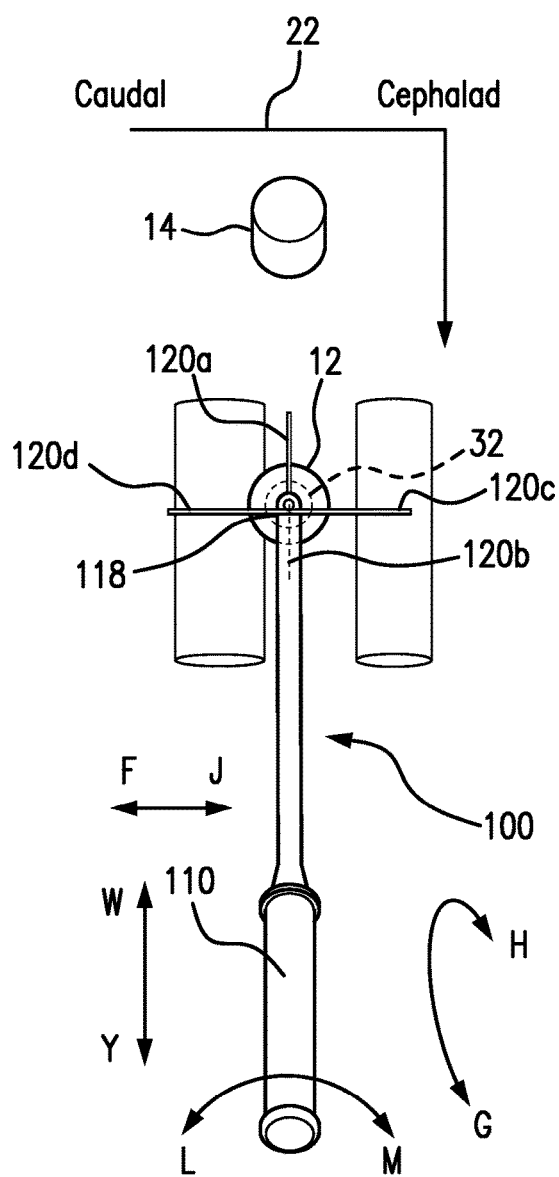
Figure 7F:
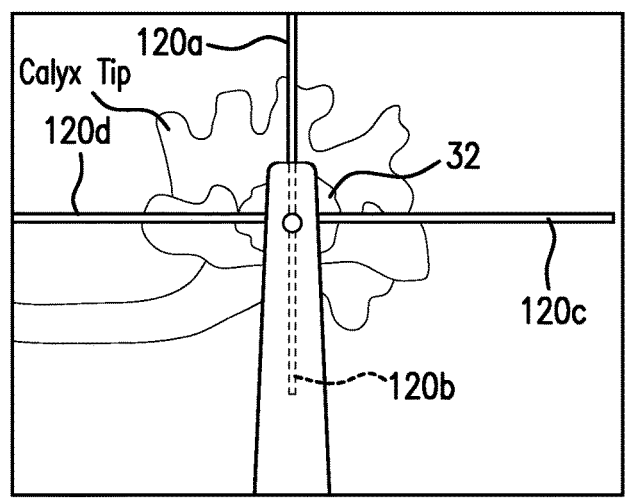

Referring to FIG. 7E, in use, and by way of example, the patient may be placed in a prone position and the C-arm rotated to the C-arm 30,0 position 12 to image the target kidney. The needle guide 100 may then be positioned on the patient's flank with the handle 110 held horizontally and perpendicular to the spine 22 to orient the crosshairs 120a-d relative to the patient and C-arm. Under fluoroscopic imaging, the needle guide 100 may be moved in the W and/or Y directions such that crosshairs 120c-d intersect the first calyx 32. FIG. 7F provides a schematic representation of crosshairs 120c-d intersecting the first calyx 32. The handle 110 may be concurrently or sequentially moved such that crosshair 120a intersects the first calyx 32, e.g., an intersection between a longitudinal axis of crosshairs 120c-d and a longitudinal axis of crosshairs 120a-b intersect the first calyx. With the crosshairs 120a-d aligned with the first calyx 32, a position of the handle 110 may be adjusted until the lumen 118 aligns with the C-arm 30,0 and the first calyx 32. Proper alignment with the first calyx 32 may be verified when the "bullseye" (e.g., radiopaque portion of the elongate shaft 112 surrounding the radiolucent silicone core and lumen 118) is visualized on the fluoroscopic image overlapping or intersecting the first calyx 32. Throughout the medical procedure, the C-arm may be intermittently turned on to image the target calyx and/or orient the needle guide 100, and then turned off to minimize exposure of the patient and/or medical professional to radiation.

In various embodiments, the "row," "pitch" and/or "yaw" of the needle guide 100 may be adjusted by rotating the handle 110 about a point defined by the intersection of crosshairs 120a-d (e.g., point A) at the distal end of the elongate shaft 112. For example, at the C-arm 30,0 position, a "row" of the needle guide 100 may be adjusted by rotating the handle 110 about the horizontal axis through point A in a direction perpendicular to arrows L and M, and a "pitch" of the needle guide 100 may be adjusted by rotating the handle 110 about the horizontal axis through point A in a direction perpendicular to direction of arrows G and H. The "yaw" (e.g., twist or oscillation about a vertical axis) of the needle guide 100 may be adjusted by moving to the C-arm 0,0 position, and moving the handle 110 about the vertical axis through point A in the direction of arrows F and J. In one embodiment, once a "bullseye" is achieved relative to the pitch and row adjustments, the C-arm may be rotated back to the A/P view (e.g., C-arm 0,0) to verify and/or adjust the proper yaw. If the yaw is proper, e.g., crosshair 120a intersects the first calyx 32, the access needle may be introduced into the lumen 118 and advanced through the patient's skin and flank towards the first calyx 32.

With the C-arm in the A/P view, the access needle may follow along the line indicated by crosshair 120a on the fluoroscopic image. As discussed above, in one embodiment a cross-sectional diameter of crosshair 120a may be less than (e g, thinner than) a cross-sectional diameter of the access needle to prevent crosshair 120a from completely obscuring (e.g., hiding) the access needle. The access needle may be distally advanced until the sharpened distal tip is visualized entering the first calyx 32.

Proper placement of the access needle within the first calyx 32 may be confirmed by urine exiting through the access needle lumen after then stylet has been removed. A guidewire may be inserted through the access needle into the target calyx, and the access needle removed from the patient. A dilator may then be introduced over the guidewire and positioned within the first calyx. A sheath may then be introduced over the dilator to allow a medical professional to introduce medial tools, e.g., to remove obstructions, including kidney stones.

Figure 8A:
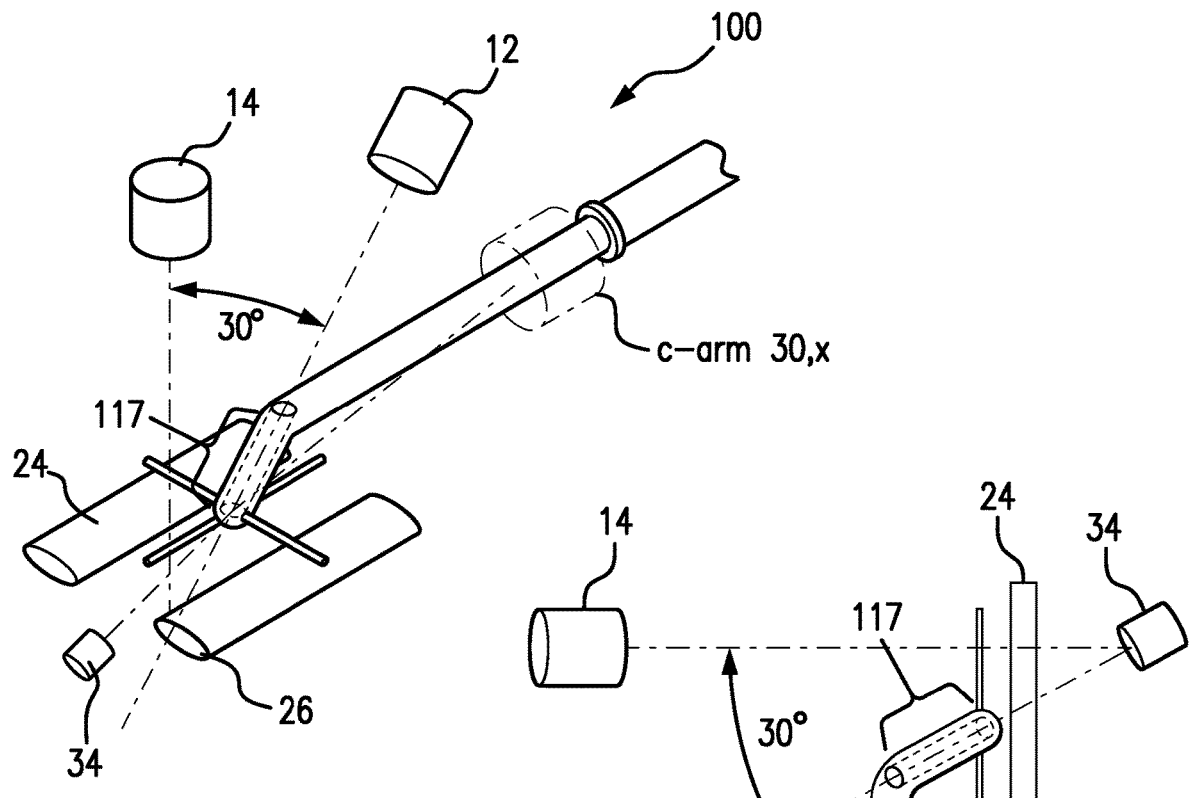
Figure 8B:
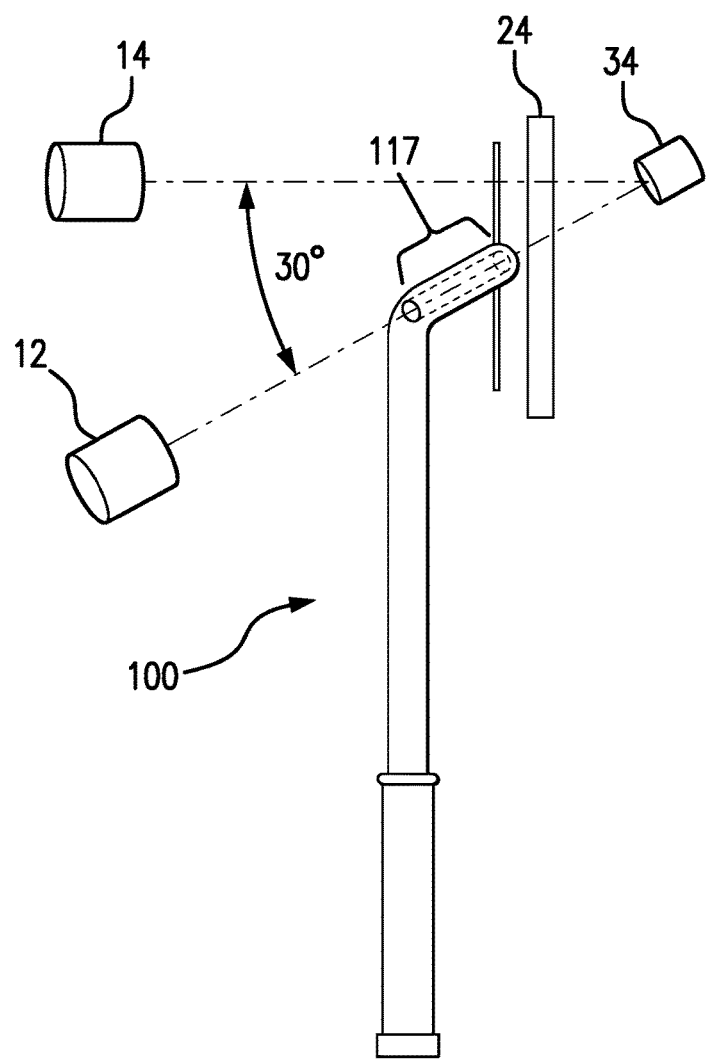

FIGS. 8A-8D provide exemplary steps involved in accessing an obstructed calyx using a needle guide 100, in accordance with one embodiment of the present disclosure. FIG. 8A provides a perspective view of a second calyx 34 that is obstructed by the eleventh rib 24. The projected needle path to the obstructed second calyx 34 may be established by an X-ray energy beam emitted from a C-arm rotated between the C-arm 0,0, C-arm 30,0, C-arm 30,X and C-arm 0,-X positions. As depicted in the perspective side view of FIG. 8B, positions C-arm 0,0 and C-arm 30,0 may be separated by an angle of approximately 30° in the lateral direction. This angle may substantially align with the 30° angle of the distal portion 117 of the elongate shaft 112 when the needle guide 100 is held in a horizontal position. As depicted in the anterior/posterior (A/P) view of FIG. 8C, as viewed from the C-arm 0,0 position, crosshair 120a of the needle guide 100 does not intersect the second calyx 34, but is instead parallel to the second calyx 34.

Referring to FIG. 8D, in use, and by way of example, the patient may be placed in a prone position and the C-arm rotated to the C-arm 30,0 position to image the target kidney. The needle guide 100 may then be positioned on the patient's flank, with the handle 110 held horizontally and perpendicular to the spine 22 to orient the crosshairs 120a-d relative to the patient and C-arm. Under fluoroscopic imaging, the needle guide 100 may be moved in the W and/or Y directions such that crosshairs 120c-d intersect the first calyx 32. The handle 110 may be concurrently or sequentially moved such that crosshair 120a is positioned to the left (or right) of the obstruction (e.g., eleventh rib 24). The C-arm may then be rotated in a caudal direction while remaining in the 30° lateral plane to an angle -X such that crosshair 120a is visualized intersecting the second calyx 34. The projected path for the access needle may then verified to be unobstructed by visually determining if any intersection exists between crosshair 120a and the eleventh rib 24. A position of the handle 110 may be adjusted until the lumen 118 aligns with the C-arm 30,0 position and the second calyx 34. Proper alignment with the second calyx 34 may be verified when the "bullseye" (e.g., radiopaque portion of the elongate shaft 112 surrounding the radiolucent silicone core and lumen 118) is visualized on the fluoroscopic image overlapping or intersecting the second calyx 34.

In various embodiments, the "row," "pitch" and/or "yaw" of the needle guide 100 may be adjusted by rotating the handle 110 about a point defined by the intersection of crosshairs 120a-d (e.g., point A) at the distal end of the elongate shaft 122. For example, at the C-arm 30,0 position, a "row" of the needle guide 100 may be adjusted by rotating the handle 110 about the horizontal axis through point A in a direction perpendicular to arrows L and M, and a "pitch" of the needle guide 100 may be adjusted by rotating the handle 110 about the horizontal axis through point A in a direction perpendicular to arrows G and H. The "yaw" (e.g., twist or oscillation about a vertical axis) of the needle guide 100 may be adjusted by moving to the C-arm 30,0, and moving the handle 110 about vertical axis through point A in the direction of arrows F and J. In one embodiment, once a "bullseye" is achieved relative to the pitch and row adjustments, the C-arm may be rotated to the C-arm 0,-X position to verify and/or adjust the proper yaw. If the yaw is proper, e.g., crosshair 120a intersects the second calyx 34, the access needle may be introduced into the lumen 118 and advanced through the patient's skin and flank towards the second calyx 34.

With the C-arm at the C-arm 0,-X position, the access needle may follow the image of crosshair 120a. As discussed above, in one embodiment a cross-sectional diameter of crosshairs 120a-d may be less (e.g., thinner) than a cross-sectional dimension of the access needle to prevent crosshair 120a from completely obscuring (e.g., hiding) the access needle. The access needle may be distally advanced until the sharpened distal tip of the access is needle is visualized entering the target calyx 34. Proper placement of the access needle within the second calyx 34 may be confirmed by urine exiting through the needle lumen after then stylet has been removed.

In one embodiment, a medical device of the present disclosure may include first 120a-d and second 120e-h sets of crosshairs to orient the needle guide 100, as discussed above. In certain medical procedures, including a medical procedure which requires gaining access to an obstructed calyx, the tendency of one or more of the first set of crosshairs 120a-d to bend or deflect when pressed against the patient's skin may prevent or hinder accurate alignment with the target calyx. A second set of crosshairs 120e-h, which do not contact the surface of the patient's skin, may provide an additional reference point to systematically align the lumen 118 and/or access needle 150 with the target calyx. In various embodiments, the systematic alignment of the first and second set of crosshairs may eliminate the need to rotate the C-arm between the 0,0 and 30,0 positions multiple times to achieve proper alignment with the target calyx. For example, with the C-arm in the C-arm 30,0 position, an unobstructed calyx may be accessed by orienting the crosshairs 120a-d using the steps outlined above. The handle 110 may first be moved as necessary to visually align crosshairs 120e and 120f with respective crosshairs 120a and 120b on the fluoroscopic image, and moved again as necessary to visually align crosshairs 120g and 120h with respective crosshairs 120c and 120d on the fluoroscopic image. As explained above, the shorter length and/or narrower width of the second set of crosshairs 120e-h, as compared to the first set of crosshairs 120a-d, may allow both sets of crosshairs to be visualized simultaneously. If any of the second sets of crosshairs 120e-h do not overlap with the corresponding first set of crosshairs 120a-d, the pitch, row and/or yaw of the handle 110 may be adjusted, as discussed above. For example, if crosshairs 120a-d appear in an offset or parallel arrangement relative to crosshairs 120e-

*h*, the pitch and/or row may need to be adjusted. If crosshairs 120*a-d* appear in a non-parallel (e.g., convergent or divergent) arrangement relative to crosshairs 120*e-h*, the yaw may need to be adjusted. Alignment of crosshairs 120*a* and 120*e* may indicate that the lumen 118 is properly aligned between the target calyx and C-arm 30,0 along a horizontal plane, without any need to further adjust a pitch (e.g., in the H or G direction) of the needle guide 100. Alignment of crosshairs 120*c-d* and 120*g-h* may indicate that the lumen 118 is properly aligned with the target calyx and C-arm 30,0 along a vertical plane, without any need to further adjust a row (e.g., in the L or M direction) of the needle guide. Similarly, at the C-arm 30,–X position, an obstructed calyx may be accessed by orienting crosshairs 120*a-d* using the steps outlined above, and moving the handle 110 as necessary to visually align crosshairs 120*a-d* and 120*e-h* to appear as a single set of overlapping crosshairs on the fluoroscopic image.

In use and by way of example, a medical professional may position a needle guide 200, 300 of the present disclosure on or above a patient's flank (e.g., between the eleventh and twelfth ribs) in the presence of a beam of X-ray energy emitted from a C-arm at position C-arm 30,0. Once the puncture site on the patient's flank is established, the medical professional may move the handle 110, 210 while maintaining the base 230, or combined first and second base portions 318, 328, in contact with the patient's skin. The handle 110, 210 may be moved as necessary until the bullseye (e.g., formed by access needle 150 and radiopaque base 230) aligns with the target calyx on the fluoroscopic image. With the proper angle to the needle trajectory established, the C-arm may be moved to position C-arm 0,0 to establish the distance between the patient's skin and the target calyx. The medical professional may then advance the access needle the required distance into the target calyx. Proper placement of the access needle within the target calyx may be confirmed by urine exiting through the needle lumen after then stylet has been removed. In various embodiments, a needle guide 200, 300 of the present disclosure may further include first or first and second sets of crosshairs to align/orient the needle guide with the target calyx, as discussed above.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A medical device, comprising:
    an elongate shaft having a longitudinal axis; and
    a first set of elongated crosshairs, each crosshair being linear and extending radially outwardly away from a distal end of a distal portion of the elongate shaft, each crosshair being configured to individually and independently flex when pressed against a patient's skin;
    wherein a portion of the distal portion of the elongate shaft, and the first set of crosshairs, comprise a radiopaque material.

2. The medical device of claim 1, wherein the first set of crosshairs includes a first crosshair and a second crosshair extending along a plane parallel to the longitudinal axis of the elongate shaft, and a third crosshair and a fourth crosshair extending along a plane perpendicular to the longitudinal axis of the elongate shaft.

3. The medical device of claim 2, further comprising a second set of crosshairs including a fifth crosshair and a sixth crosshair extending along a plane parallel to the longitudinal axis of the elongate shaft, and a seventh crosshair and an eighth crosshair extending along a plane perpendicular to the longitudinal axis of the elongate shaft.

4. The medical device of claim 1, furthering comprising a second set of crosshairs disposed about the distal end of the distal portion of the elongate shaft, extending radially outwardly away from the elongate shaft from a location proximal to the first set of crosshairs.

5. The medical device of claim 4, wherein a width and a length of the second set of crosshairs is less than a width and a length of the first set of crosshairs.

6. The medical device of claim 4, wherein at least one of the first set of crosshairs or the second set of crosshairs comprises a radiopaque material.

7. The medical device of claim 1, wherein:
    the distal portion of the elongate shaft is angled relative to the longitudinal axis of the elongate shaft; and
    a lumen extends through the angled distal portion.

8. The medical device of claim 7, wherein the lumen comprises a radiolucent silicone core.

9. The medical device of claim 8, wherein the radiolucent silicone core is configured to receive an outer surface of an access needle.

10. The medical device of claim 1, wherein the first set of crosshairs are formed of a flexible material allowing each crosshair to individually flex when pressed against a patient's skin.

11. The medical device of claim 1, wherein each crosshair is movable with respect to the other crosshairs.

12. The medical device of claim 1, wherein each crosshair can individually flex.

13. A medical device, comprising:
    an elongate shaft having a proximal end, a distal end, a distal portion adjacent the distal end, a longitudinal axis between the proximal end and the distal portion, and a lumen extending through the distal portion at an angle with respect to the longitudinal axis of the elongate shaft and configured to receive an access needle therethrough; and
    a first set of crosshairs, each crosshair being linear and extending radially outwardly away from the distal portion and the lumen of the elongate shaft, wherein each crosshair can individually flex.

14. The medical device of claim 13, wherein the first set of crosshairs includes a first crosshair and a second crosshair extending along a plane parallel to the longitudinal axis of the elongate shaft, and a third crosshair and a fourth crosshair extending along a plane perpendicular to the longitudinal axis of the elongate shaft.

15. The medical device of claim 13, furthering comprising a second set of crosshairs disposed about the distal end of the distal portion of the elongate shaft, extending radially outwardly away from the elongate shaft from a location proximal to the first set of crosshairs.

16. The medical device of claim 15, wherein a width and a length of the second set of crosshairs is less than a width and a length of the first set of crosshairs.

17. The medical device of claim 15, wherein at least one of the first set of crosshairs or the second set of crosshairs comprises a radiopaque material.

18. The medical device of claim 13, wherein:
the distal portion of the elongate shaft is angled relative to the longitudinal axis of the elongate shaft.
19. The medical device of claim 13, wherein the lumen comprises a radiolucent silicone core.

* * * * *